United States Patent [19]

Fasnacht

[11] Patent Number: 4,818,225
[45] Date of Patent: Apr. 4, 1989

[54] ORTHODONTIC ELASTIC BAND AND TREATMENT METHOD

[76] Inventor: Jeffery L. Fasnacht, 4956 Douglas Ave., Racine, Wis. 53402

[21] Appl. No.: 23,716

[22] Filed: Mar. 9, 1987

[51] Int. Cl.$^4$ ............................................. A61C 7/00
[52] U.S. Cl. ....................................... 433/18; 433/11; 206/805
[58] Field of Search ................... 206/805; 433/11, 15, 433/80, 18

[56] References Cited

U.S. PATENT DOCUMENTS 3,205,576  9/1965  Wallshein ............................. 433/18
3,600,807  8/1971  Sipos .

OTHER PUBLICATIONS

TP Laboratories Publication–Elastomerics & Elastics–2 pp.–Received in Pat. Off., Feb. 1986.

Primary Examiner—Carroll B. Dority, Jr.
Attorney, Agent, or Firm—Peter N. Jansson

[57] ABSTRACT

An orthodontic elastic band having an orally-acceptable elastomeric material which is natural, natural-synthetic or synthetic rubber or theromplastic polymeric material, and a flavoring substance uniforming dispersed therein. Preferred embodiments have 0.1–10 parts by weight, and most preferably 1–5 parts, of the flavoring substance per 100 parts elastomeric material. Preferred flavoring substances are flavoring oils, and the preferred elastomeric materials are the rubbers, most preferably natural rubber. Also disclosed is an orthodontic treatment method including releasing a flavoring substance from an intraoral elastic band by contact thereof with the oral environment to encourage frequent elastic band replacement.

19 Claims, No Drawings

ORTHODONTIC ELASTIC BAND AND TREATMENT METHOD

FIELD OF THE INVENTION

This invention is related generally to tensioning devices for use in orthodontia. More specifically, this invention is related to intraoral elastic bands of the type replaceably placed in tension by the patient, and to treatment methods using intraoral elastic bands.

BACKGROUND OF THE INVENTION

Intraoral elastics, sometimes referred to as orthodontic "elastic bands," have been used in the orthodontic profession for many years. The term "intraoral elastic bands," as used herein and as commonly understood, refers to elastic bands which are replaceably placed in tension between securement points, usually hooks, in the mouth. Such elastic bands are replaced by the patient frequently, preferably several times each day.

Intraoral elastic bands are usually in the form of endless loops, but this invention may apply to other forms of elastic bands in which strands are replaceably placed in tension between hooks in the mouth. In the typical endless loop form, various strengths and sizes of loops are used depending on the geometry of the orthodontic need, that is, the distance between hooks, and other factors.

Intraoral elastic bands, which are stretched between hooks secured to the teeth, apply directional force to the teeth. The elastic force of the intraoral elastic bands is applied in manner urging teeth to move from their positions of malocclusion to their non-orthodontic normal positions. Moving teeth is the sole purpose of orthodontic elastic bands.

Frequent replacement of intraoral elastic bands by the patient is essential to maintaining the intended level of corrective force on an improperly located tooth. This is due to the fact that the elastic strength of intraoral elastic bands decays rapidly in the oral environment.

The weakening of the elastic force of intraoral elastic bands occurs as water and acids in the mouth are absorbed into the elastic band. Weakening begins upon first exposure within the oral environment and continues. When the liquids in the mouth are absorbed throughout the elastic band, its elastic strength is at a much lower level than during the period immediately after placement in the mouth.

More specifically, the elastic modulus of certain common orthodontic elastic bands typically decays about 40–60 percent during the first two hours after placement in tension in the mouth of the patient. The corrective force applied by such elastic band is thus substantially reduced over this short initial period of use.

Many patients, however, do not replace their orthodontic elastic bands until hours after the loss of most of their elastic strength. Therefore, the corrective pressure applied on the teeth of such patients, by a series of elastic bands, is applied with substantial variation and with extended interruptions.

Infrequent and irregular replacement of intraoral elastic bands is a common problem in the field of orthodontics. This can greatly extend the length of the period of orthodontic care for the patient. In many cases, the period of orthodontic treatment extends for months beyond what would otherwise be necessary.

Improving regularity and faithfulness of elastic band replacement is very helpful in orthodontic treatment. Even more important is increasing the frequency of a patient's elastic band replacement.

Many patients replace their orthodontic elastic bands at specific times of the day, for example, upon rising in the morning and retiring at night, or upon the occurrence of other regular events, such as meals. Others are less faithful. However, even following a fairly rigorous schedule of changes, three or four times daily, the amount of corrective force applied to the teeth is insufficient over long periods and varies too much. More frequent replacement would be desirable.

Few patients are willing or able to remember to change orthodontic elastic bands frequently enough for the most effective application of corrective force. Children may be very lax in making required changes on time. They usually consider anything having to do with their orthodontic treatment to be a negative experience, so are often quite willing to forget or postpone the replacement of their orthodontic elastic bands.

Orthodontic elastic bands are not a particularly appealing thing to place in one's own mouth. And, there is nothing about the act of replacing orthodontic elastic bands which makes it a pleasant experience, or in any sense a rewarding experience.

Efforts to increase the frequency of elastic band replacement and/or at least to encourage compliance with some sort of schedule have not been particularly successful. So the typical course of orthodontic treatment for a patient has remained longer than is necessary.

OBJECTS OF THE INVENTION

It is an object of this invention to provide an improved intraoral orthodontic elastic band overcoming some of the problems and shortcomings of the prior art including those mentioned above.

Another object of this invention is to provide an orthodontic elastic band providing an inducement for replacement.

Another object of this invention is to provide a pleasantly flavored intraoral orthodontic elastic band which encourages faithful elastic band replacement by the patient.

Still another object of this invention is to provide a pleasantly flavored intraoral orthodontic elastic band which encourages more frequent elastic band replacement by the patient.

Another object of this invention is to provide an orthodontic elastic band capable of imparting a pleasant flavor to the mouth of the patient during an initial period commensurate with the initial period during which its elastic strength is sufficient to provide effective corrective force.

Another object of this invention is to provide an improved method of orthodontic treatment of the type utilizing frequently replaceable elastic bands.

These and other important objects will be apparent from the descriptions of this invention which follow.

SUMMARY OF THE INVENTION

This invention is an improved intraoral orthodontic elastic band for use in tension and a related improved method of orthodontic treatment. The invention overcomes certain problems and shortcomings of the prior art.

Using the intraoral orthodontic elastic bands and the method of this invention encourages greater regularity and increased frequency of elastic band replacement by patients. As a result, the length of the entire period of orthodontic treatment may be reduced.

The intraoral elastic band of this invention is made of an orally-acceptable elastomeric material selected from the group consisting of natural rubber, natural-synthetic rubber, synthetic rubber, thermoplastic polymeric materials, and blends thereof, chosen to have suitable physical properties for application of corrective force when used in tension, and a flavoring substance uniformly dispersed within the elastomeric material.

The method of this invention involves inducing frequent repetition of removal and replacement of intraoral elastic bands by the patient, by providing a supply of elastic bands having a flavoring substance therein which is releasable in an oral environment and releasing the flavoring substance by contact with the oral environment. Repositioning of teeth from positions of malocclusion to their non-orthodontic position is thereby accelerated.

In preferred forms, the method includes substantially reducing or terminating the release of flavoring after a predetermined period which is commensurate with the period of substantial initial reduction in the elastic strength of the elastic bands. Such reduction or termination of flavor release provides an added inducement to replace the elastic bands. Such substantial reduction in release occurs upon absorption of oral fluids throughout the elastic band.

The flavoring substance is preferably present in an amount of about 0.1 to 10 parts by weight per 100 parts of elastomeric material, depending on various factors including the elastomeric material used and the flavoring substance used. Generally speaking, amounts of flavoring substance less than about 0.1 parts per 100 parts elastomeric material tend to provide insufficient flavoring to be of value. Amounts of flavoring substance beyond about 10 parts per 100 parts elastomeric material tend to unacceptably harm the physical properties of elastomeric material, by reducing the tensile strength, elongation and elasticity.

Preferred embodiments include about 1 to 5 parts by weight flavoring substance per 100 parts elastomeric material. In this rang, the properties of the elastomeric material generally will remain substantially unimpaired, and flavoring properties are good. Particularly preferred embodiments utilize between 2 and 4 parts flavoring substance per 100 parts elastomeric material.

A wide variety of food-grade flavoring substances are useful in this invention. Such substances may be used in either liquid or powder form in making the elastic bands of this invention. Flavoring substances are of a variety of chemical families well known for having flavoring characteristics. The flavoring substance is preferably chosen to provide a very pleasant, familiar and distinct flavor, such as peppermint, spearmint and the like.

The flavoring substances are preferably selected from the group consisting of natural and artificial flavoring oils and blends thereof. Flavoring oils are often distillates of natural extracts or are synthesized materials.

Examples of the preferred flavoring oils are: Givaudan F8266, a blend of natural and artificial spearmint oils, available from Givaudan Company, Clifton, N.J.; Givaudan F9114, a blend of natural and artificial peppermint-spearmint oils; natural peppermint oils; and natural spearmint oils. Other examples of acceptable flavoring substances include artificial sweeteners, such as aspartame powder, and powdered synthetic flavorings. A wide variety of other acceptable flavoring substances are available.

Even though the intraoral elastic bands of this invention, with their flavoring substances dispersed therein, are used in tension, it has been found that they apply corrective force in a very favorable manner and over a period comparable to elastic bands without such additives. The elastic characteristics are maintained, even while important advantages are obtained from the flavoring.

As noted, the elastomeric material is selected from the group consisting of natural rubber, natural-synthetic rubber, synthetic rubber, thermoplastic polymeric materials, and blends thereof. In preferred embodiments, the elastomeric material is a natural, natural-synthetic or synthetic rubber, or blend thereof. The most preferred elastomeric material is natural rubber.

Natural rubber (polyisoprene) is a material widely used in elastic bands. Natural-synthetic rubber is generally similar to natural rubber. Synthetic rubbers would include neoprene, butyl and polybutadiene. Examples of acceptable thermoplastic polymeric materials includes plasticized polyethylene and polyurethanes, chosen to have suitable physical properties for elastic bands.

Additional constituents may in some cases be used for particular purposes, such as to provide a vehicle for a flavoring powders or to improve the elastomeric qualities of the intraoral elastic band. For example, vegetable oils and mineral oils may improve the elastomeric qualities. Such oils may be included by blending of such oils with flavoring oils. Other variations and additions may be used.

In certain embodiments using flavoring oils, it is necessary to uniformly mix the oil or oils into a latex during manufacture of the elastic bands. In such cases, the use of emulsifying agents is helpful.

Acceptable surfactants for use as emulsifiers in making the preferred orthodontic elastic bands, having natural, natural-synthetic or synthetic rubbers, include anionic or nonionic surfactants and anionic-nonionic surfactant mixtures which are acceptable for contact in the mouth. Examples of suitable anionic surfactants include: sorbitan esters, sulfonates and oleates. Suitable nonionic surfactants include diglycerides, nonyl phenol ethoxylate, polyethylene glycol ethers and alkylaryl polyether alcohol.

In preparing such preferred orthodontic elastic bands, the flavoring oils can be emulsified in water with suitable surfactants, such as the sorbitan esters, using high speed propeller type mixers, and then blended into the latex compound.

A stabilizer, or protective colloid, such as casein, gelatin, various starches and alginates are preferably present in an amount from 0.25 to 1.0 parts for 100 parts rubber. The emulsifier is also preferably present in an amount from 0.25 to 1.0 parts per 100 parts rubber.

Various methods may be used to make the orthodontic elastic bands of this invention. As is common in the elastic band art, long tubes of material are first made and then cut by an automatic cutting device to form the elastic bands.

The long tubes may be made by one of several processes, including a dipping process or an extruding process. In the dipping process, the curing is typically carried out using continuous hot air tunnels, radiant heat, such as may be applied from infrared heaters, and/or boiling water. In the extruding process, a hot liquid cure or fluidized bed may be used.

The most preferred method of making the tubes involves a dipping process which is carried out as follows:

A liquid rubber latex is placed in a suitable tank or other mixing vessel which has an agitator or other mixing device in it. Suitable vulcanizing agents, accelerators, activators, emulsion stabilizers, and anti-oxidants are blended into the natural rubber latex. This is carried out in known manner.

An intermediate is formed in another vessel by mixing the flavoring oil or a blend of flavoring oils together with water and suitable emulsifiers. Such intermediate is then added to the latex mixture and blended thoroughly.

A flexible mandril, for example, a silicone snake having a generally uniform outer diameter which is equal to the intended, non-expanded inner diameter of the elastic band to be made, is dipped repeatedly into the above final blend. Heat is applied to the mandril between dips, each time it emerges from the blend. The heat is preferably applied by infrared heaters.

About 0.002 inch of material thickness is added to the mandril per dip, the amount depending on various factors, primarily including the nature of the blend. For an orthodontic elastic band having about an 0.032 inch wall dimension, 16 dips are required. After the last dip and the brief period of heat application to gel the last dip, the formed tube is stripped from the mandril, usually by applying high-pressure air at one end of the mandril.

This tube is then passed through a bromine bath, with the ends of the tube preferably being tied such that only the outside surface of the tube is exposed to the bromine bath. The bromine bath serves to react with any unsaturated double bonds to reduce tackiness on the outside of the tube. Then, the tube is passed into boiling hot water for a final cure, lasting about 45 minutes. After removal from the boiling water, the tube is dried and is ready for cutting, using automatic cutting equipment, as noted.

The extrusion method, which typically uses a very high temperature (140–200 degrees C.) cure, has the advantage of higher production rates. Such a process may be carried out as follows:

Crepe rubber is compounded in a Banbury type mixer or a two-roll mill. After suitable mixing the rubber is run through an extruder having an extrusion opening with the dimensions required in the finished elastic band. A tube of material flows out of the extruder into a high temperature liquid for curing.

The high temperature liquid may one of several liquids, such as polyglycols, certain silicone fluids, or eutectic mixtures of potassium nitrate, sodium nitrate and sodium nitrite. In such hot liquids, curing occurs rapidly. The use of such hot liquids for curing also prevents volatilization of important fractions of the flavoring oils.

An alternative to the use of such high temperature liquid curing is the use of fluidized beds, which are a volume of small particles of glass beads or the like suspended in a stream of heated air. The advantage of using a fluidized bed is that it avoids the build-up of chemical residues on the tubes and thus on the orthodontic elastic bands cut from such tubes. For this reason, the use of fluidized beds may be preferred over high temperature liquid curing.

In any extruding process, regardless of the exact cure method used, passing the tube through a bromine bath is preferred in order to eliminate unsaturated double bonds. In such cases, however, the subsequent boiling step serves primarily only to remove the bromine, rather than as a final curing step.

Other processing methods for the preparation of tubing may be used instead. In each case, the cutting step follows.

EXAMPLE 1

An elastic band having a 0.032 inch wall dimension and a 0.25 inch unexpanded diameter (when in circular form) is produced using the dipping and cutting methods described above with a dipping blend made with the following:

| Ingredient | Amount (in parts) |
| --- | --- |
| Polyisoprene latex | 100.00 |
| Anionic stabilizer | 0.50 |
| Dibutyl ammonium oleate | 0.75 |
| Antioxidant | 2.00 |
| Zinc oxide | 0.50 |
| Sulfur | 1.50 |
| Accelerator | 0.50 |
| Givaudan F8266 flavoring | 2.00 |

The Givaudan F8266 is a flavoring substance which is an artificial spearmint oil. The intraoral elastic bands provide good corrective force in tension and an attractive flavor which encourages regular and frequent replacement by the patient.

EXAMPLE 2

An elastic band having a 0.032 inch wall dimension and a 0.125 inch unexpanded diameter is made as in Example 1, using the same ingredients except that the Givaudan F8266 flavoring is replaced by 1.0 parts of Givaudan F9114 flavoring, a flavoring substance which is a peppermint blend. The intraoral elastic bands provide good corrective force in tension and flavoring at a reasonable level.

EXAMPLE 3

An elastic band having a 0.032 inch wall dimension and a 0.25 inch unexpanded diameter is made as in Example 1, but using the following

| Ingredient | Amount (in parts) |
| --- | --- |
| Polyisoprene latex | 100.00 |
| Anionic stabilizer | 0.50 |
| Dibutyl ammonium oleate | 0.75 |
| Antioxidant | 2.00 |
| Zinc oxide | 0.50 |
| Sulfur | 1.50 |
| Accelerator | 0.50 |
| Givaudan F8266 flavoring | 5.00 |

The intraoral elastic bands provide good corrective force in tension and strong flavor.

EXAMPLE 4

An elastic band having a 0.032 inch wall dimension and a 0.5 inch unexpanded diameter is made as in Example 1, but using the Givaudan F8266 flavoring at 0.5 parts. The intraoral elastic bands provide an attractive spearmint flavor in the oral environment.

EXAMPLE 5

An elastic band having a 0.032 inch wall dimension and a 0.25 inch unexpanded diameter is made using the extruding method as described above, curing in high temperature range of 140–180 degrees C., using the following:

| Ingredient | Amount (in parts) |
| --- | --- |
| Natural rubber (pale crepe) | 100.00 |
| Stearic acid | 0.75 |
| Zinc oxide | 0.75 |
| Antioxidant | 1.00 |
| Accelerator | 1.00 |
| Curing agent | 1.25 |
| Givaudan F8266 | 0.20 |

The intraoral elastic bands provides acceptable corrective force in tension and an attractive flavor.

EXAMPLE 6

An elastic band having a 0.032 inch wall dimension and a 0.25 inch unexpanded diameter is made using the extruding method as described, curing in a fluidized bed, using the formulation of Example 5. The resulting product is similar.

EXAMPLE 7

A flavored elastic band having a 0.032 inch wall dimension and a 0.25 inch unexpanded diameter is made using thermoplastic polyester urethane rubbers, for example, an Estane-type available from B. F. Goodrich Company, Akron, Ohio, utilizing known sulfur or peroxide vulcanizing systems with activators, processing aids, and one of the two Givaudan flavoring substance mentioned above. In some cases, carboiimides may be used to improve the hydrolytic stability of the polyester.

As an alternative, thermoplastic polyether-based urethane rubbers are used, such as Adiprene, available from DuPont Company, Wilmington, Del., or Texin, available from Mobay Chemical Company, St. Louis, Mo., using the same vulcanizing systems and techniques.

Such urethane compounds are extrudable as finished tubes not requiring a high-temperature final cure prior to being cut into flavored elastic bands. The urethanes provide flavored intraoral elastic bands with excellent abrasion resistance and elastic properties, high tensile strength, and flavor which is readily discernible.

While the principles of this invention have been described in connection with specific embodiments, it should be understood clearly that these descriptions are made only by way of EXAMPLE and are not intended to limit the scope of the invention.

What is claimed is:

1. An intraoral orthodontic elastic band for replaceable use in tension comprising:
   an orally-acceptable elastomeric material selected from the group consisting of natural rubber, natural-synthetic rubber, synthetic rubber, thermoplastic polymeric materials, and blends thereof, having suitable physical properties; and
   a food-grade flavoring substance substantially uniform throughout the elastomeric material as an in situ constituent of elastic-band formation from a homogeneous mixture of said elastomeric material and said flavoring substance, whereby without compromising elastomeric force properties the elastic band provides flavor release in an intraoral environment during an extended period which is substantially commensurate with the period of substantial initial reduction in elastic band strength.

2. The intraoral orthodontic elastic band of claim 1 wherein the flavoring substance is present in an amount of about 0.1 to 10 parts by weight per 100 parts of elastomeric material.

3. The intraoral orthodontic elastic band of claim 2 wherein the flavoring substance is present in an amount of about 1 to 5 parts by weight per 100 parts of elastomeric material.

4. The intraoral orthodontic elastic band of claim 1 wherein the flavoring substance is selected from the group consisting of natural and artificial flavoring oils and blends thereof.

5. The intraoral orthodontic elastic band of claim 4 wherein the flavoring oil is present in an amount of about 0.1 to 10 parts by weight per 100 parts of elastomeric material.

6. The intraoral orthodontic elastic band of claim 5 wherein the flavoring oil is present in an amount of about 1 to 5 parts by weight per 100 parts of elastomeric material.

7. The intraoral orthodontic elastic band of claim 1 comprising:
   the elastomeric material being selected from the group consisting of the natural, natural-synthetic and synthetic rubbers, and blends thereof;
   the flavoring substance being selected from the group consisting of natural and artificial flavoring oils and blends thereof; and
   an emulsifying agent present in an amount sufficient to disperse the flavoring oils uniformly in the latex of the rubber during production.

8. The intraoral orthodontic elastic band of claim 7 wherein the elastomeric material is natural rubber.

9. The intraoral orthodontic elastic band of claim 7 wherein the flavoring oil is present in an amount of about 0.1 to 10 parts by weight per 100 parts of elastomeric material.

10. The intraoral orthodontic elastic band of claim 9 wherein the flavoring oil is present in an amount of about 1 to 5 parts by weight per 100 parts of elastomeric material.

11. The intraoral orthodontic elastic band of claim 10 wherein the elastomeric material is natural rubber.

12. In a method of orthodontic treatment of the type including gradually moving a tooth of a patient from a position of malocclusion to its non-orthodontic normal position by repeatedly (a) placing an unused elastic band in tension between hooks secured with respect to the teeth of the patient, (b) removing and discarding such elastic band, and (c) thereafter immediately placing another similar unused elastic band in tension between the hooks, the improvement comprising inducing frequent repetition of steps b and c by:
   providing a supply of elastic bands having an elastomeric material and a food-grade flavoring substance substantially uniform throughout the elastomeric material as an in situ constituent of elastic-band formation from a homogeneous mixture of said elastomeric material and said flavoring substance, said flavor being releasable in an oral environment; and
   releasing the flavoring substance therefrom by contact with the oral environment during an extended period substantially commensurate with the period of substantial initial reduction in elastic band strength, whereby repositioning of the improperly positioned tooth is accelerated.

13. The method of claim 12 including the additional step of substantially reducing the release of flavoring substances after a predetermined period commensurate with the period of substantial initial reduction in the elastic strength of the elastic bands.

14. The method of claim 12 wherein the elastic bands comprise an orally-acceptable elastomeric material selected from the group consisting of natural rubber, natural-synthetic rubber, synthetic rubber, thermoplastic polymeric materials, and blends thereof, having suitable physical properties, said flavoring substance being uniformly dispersed within the elastomeric material.

15. The method of claim 14 including the additional step of substantially reducing the release of flavoring substances after a predetermined period commensurate with the period of substantial initial reduction in the elastic strength of the elastic bands, said substantial reduction in release occurring upon absorption of oral fluids throughout the elastic band.

16. The method of claim 14 wherein:
the elastomeric material is selected from the group consisting of the natural, natural-synthetic and synthetic rubbers, and blends thereof; and
the flavoring substance is present in an amount of about 0.1 to 10 parts by weight per 100 parts of elastomeric material.

17. The method of claim 16 wherein the flavoring substance is present in an amount of about 1 to 5 parts by weight per 100 parts of elastomeric material.

18. The method of claim 17 wherein the flavoring substance is selected from the group consisting of natural and artificial flavoring oils and blends thereof.

19. The method of claim 18 wherein the elastomeric material is natural rubber.

* * * * *